United States Patent
Gong et al.

(10) Patent No.: US 11,279,676 B2
(45) Date of Patent: Mar. 22, 2022

(54) CRYSTALLINE OF COMPOUND AS C-MET KINASE INHIBITOR AND PREPARATION METHOD THEREFOR AND USE THEREOF

(71) Applicants: CHIA TAI TIANQING PHARMACEUTICAL GROUP CO., LTD., Jiangsu (CN); ADVENCHEN LABORATORIES NANJING LTD., Jiangsu (CN)

(72) Inventors: Feng Gong, Jiangsu (CN); Ticong Huang, Jiangsu (CN); Haishan Zang, Jiangsu (CN); Shibo Zhang, Jiangsu (CN); Rui Zhao, Jiangsu (CN); Fei Liu, Jiangsu (CN)

(*) Notice: Subject to any disclaimer, the term of this patent is extended or adjusted under 35 U.S.C. 154(b) by 0 days.

(21) Appl. No.: 16/977,054

(22) PCT Filed: Mar. 1, 2019

(86) PCT No.: PCT/CN2019/076683
§ 371 (c)(1),
(2) Date: Aug. 31, 2020

(87) PCT Pub. No.: WO2019/166012
PCT Pub. Date: Sep. 6, 2019

(65) Prior Publication Data
US 2021/0047272 A1    Feb. 18, 2021

(30) Foreign Application Priority Data
Mar. 2, 2018   (CN) .......................... 201810174767.4

(51) Int. Cl.
*C07D 215/22* (2006.01)

(52) U.S. Cl.
CPC ........ *C07D 215/22* (2013.01); *C07B 2200/13* (2013.01)

(58) Field of Classification Search
CPC .......................... C07D 215/22; C07B 2200/13
See application file for complete search history.

(56) References Cited

U.S. PATENT DOCUMENTS

| | | |
|---|---|---|
| 7,667,039 B2 | 2/2010 | Garcia-Echeverria et al. |
| 8,148,532 B2 | 4/2012 | Chen |
| 9,550,781 B2 | 1/2017 | Xiao |
| 9,725,439 B2 | 8/2017 | Xiao et al. |
| 9,751,859 B2 | 9/2017 | Chen |
| 9,968,597 B2 | 5/2018 | Zhang et al. |
| 10,100,034 B2 | 10/2018 | Chen |
| 10,112,945 B2 | 10/2018 | Chen et al. |
| 10,183,017 B2 | 1/2019 | Zhang et al. |
| 10,251,876 B2 | 4/2019 | Wang et al. |
| 10,307,412 B2 | 6/2019 | Wang et al. |
| 10,730,878 B2 | 8/2020 | Chen et al. |
| 10,736,887 B2 | 8/2020 | Chen et al. |
| 2010/0105696 A1 | 4/2010 | Garcia-Echevrria et al. |
| 2012/0123126 A1* | 5/2012 | Chen .................. A61K 31/4709 546/153 |
| 2016/0326138 A1 | 11/2016 | Chen et al. |
| 2017/0174687 A1 | 6/2017 | Chen |
| 2017/0182027 A1 | 6/2017 | Wang |
| 2017/0202828 A1 | 7/2017 | Zhang |
| 2017/0304290 A1 | 10/2017 | Wang et al. |
| 2018/0002311 A1 | 1/2018 | Chen et al. |
| 2018/0201613 A1 | 7/2018 | Chen et al. |
| 2018/0235953 A1 | 8/2018 | Zhang et al. |
| 2019/0002435 A1 | 1/2019 | Chen et al. |
| 2019/0125739 A1 | 5/2019 | Chen et al. |
| 2019/0269671 A1 | 9/2019 | Wang et al. |
| 2019/0298712 A1 | 10/2019 | Wang et al. |

FOREIGN PATENT DOCUMENTS

| | | |
|---|---|---|
| CN | 101809012 | 8/2010 |
| CN | 102344438 | 2/2012 |
| CN | 103483319 | 1/2014 |
| CN | 104817497 A | 8/2015 |
| CN | 105153028 A | 12/2015 |
| WO | WO 2006/122806 | 11/2006 |
| WO | WO 2008/112407 | 9/2008 |
| WO | WO 2008/112408 | 9/2008 |

(Continued)

OTHER PUBLICATIONS

Bello, E. et al., E-3810 Is a Potent Dual Inhibitor of VEGFR and FGFR that Exerts Antitumor Activity in Multiple Preclinical Models, Cancer Research; 71(4), Feb. 15, 2011.
Eskens et al., "Phase I Dose Escalation Study of Telatinib, a Tyrosine Kinase Inhibitor of Vascular Endothelial Growth Factor Receptor 2 and 3, Platelet-Derived Growth Factor Receptor β, and c-Kit, in Patients With Advanced or Metastatic Solid Tumors." Journal of Clinical Oncology (2009), vol. 27 (25), pp. 4169-4176.
Han et al., "Anlotinib as a third-line therapy in patients with refractory advanced non-small-cell lung cancer: a multicentre, randomised phase 11 trial (AL TER0302)", 2018, British Journal of Cancer, 118(5), pp. 654-661. (Year: 2018).
International Search Report on Patentability received in International Application No. PCT/CN2019/076683, dated May 7, 2019, in 8 pages.

(Continued)

*Primary Examiner* — Timothy R Rozof
(74) *Attorney, Agent, or Firm* — Knobbe, Martens, Olson & Bear, LLP

(57) ABSTRACT

The present application falls within the field of medicinal chemistry, relates to the crystalline of a compound as a c-Met kinase inhibitor, and specifically relates to the crystalline of N-(4-((7-((1-(cyclopentylamino)cyclopropyl)methoxy)-6-methoxyquinolin-4-yl)oxy)-3-fluorophenyl)-N-(4-fluorophenyl)cyclopropane-1,1-dicarboxamide, and a preparation method therefor, a crystalline composition thereof, and a pharmaceutical composition thereof, as well as the use of the crystalline for treating diseases associated with the inhibition of growth factor receptor protein tyrosine kinase activity. The crystalline of the present application has excellent properties in at least one of the following aspects: pharmacokinetics, bioavailability, hygroscopicity, stability, solubility, purity, ease of preparation, etc.

18 Claims, 8 Drawing Sheets

(56) References Cited

FOREIGN PATENT DOCUMENTS

| WO | WO 2009/155527 | 12/2009 |
|---|---|---|
| WO | WO 2010/105761 | 9/2010 |
| WO | WO 2014/113616 | 7/2014 |
| WO | WO 2016/091168 A1 | 6/2016 |
| WO | WO 2019/166012 A1 | 9/2019 |
| WO | WO 2020/181214 A1 | 9/2020 |

OTHER PUBLICATIONS

Moreno et al., "Tyrosine Kinase Inhibitors in Treating Soft Tissue Sarcomas: sunitinib in non-GIST sarcomas," Clin Transl Oncol (2010) 12:468-472.

National Center for Biotechnology Information. PubChem Compound Database; CI D=25017 411, https://pubchem.ncbi .nlm. nih .gov/compound/25017 411 (accessed Apr. 4, 2018). (Year: 2018).

Ranson et al., British Journal of Cancer (2004), vol. 90, pp. 2250-2255. (Year: 2004).

Sala, F. et al., Development and validation of a high-performance liquid chromatography—tandem mass spectrometry method for the determination of the novel inhibitor of angiogenesis E-3810 in human plasma and its application in a clinical pharmacokinetic study, Journal of Mass Spectrometry, 2011, 46, pp. 1039-1045.

Silverman, R. "The Organic Chemistry of Drug Design and Drug Action," 2004, Elsevier, pp. 29-32.

Sun et al., "Safety, pharmacokinetics, and antitumor properties of anlotinib, an oral multi-target tyrosine kinase inhibitor, in patients with advanced refractory solid tumors", 2016, Journal of Hematology & Oncology, 9: 105; DOI 10.1186/s 13045-016-0332-8. (Year: 2016).

Taurin et al. Endometrial Cancers Harboring Mutated Fibroblast Growth Factor Receptor 2 Protein Are Successfully Treated With a New Small Tyrosine Kinase Inhibitor in an Orthotopic Mouse Model. Aug. 8, 2017 [Retrieved May 8, 2020] Retrieved from internet URL:<https://www.ncibi.nlm.nih.gov/pmc/articles/PMC5735020/pdf/igj-28-152.pdf>.

Traina et al.—Optimizing Chemotherapy Dose and Schedule by Norton-Simon Mathematical Modeling, Breast Dis (2010), vol. 31(1), pp. 1-21.

XELODA® Prescribing Information; Genentech USA, Inc.,—Xeloda, Mar. 2015.

Zhang et al., Mol Neurobiol, 2015, vol. 52, pp. 1527-1539. (Year:2015).

Zhou, Y. et al., AL3810, a multi-tyrosine kinase inhibitor, exhibits potent anti-angiogenic and ant-tumor activity via targeting VEGFR, FGFR, and PDGFR, Journal of Cellular and Molecular Medicine, vol. 16, No. 10, 2012 pp. 2321-2330.

\* cited by examiner

CRYSTALLINE OF COMPOUND AS C-MET KINASE INHIBITOR AND PREPARATION METHOD THEREFOR AND USE THEREOF

CROSS-REFERENCE TO RELATED APPLICATIONS

This application is the U.S. National Phase of International Application No. PCT/CN2019/076683, filed Mar. 1, 2019, which claims the priority and benefit of the Chinese patent application No. 201810174767.4 filed with the State Intellectual Property Office of China on Mar. 2, 2018. The disclosure of each of the foregoing applications is herein incorporated by reference in their entireties.

FIELD OF THE INVENTION

The present application falls within the field of medicinal chemistry, relates to a crystalline of a compound as a c-Met kinase inhibitor, and specifically relates to the crystalline of N-(4-((7-((1-(cyclopentylamino)cyclopropyl)methoxy)-6-methoxy-quinolin-4-yl)oxy)-3-fluorophenyl)-N-(4-fluorophenyl)cyclopropane-1,1-dicarboxamide, and a preparation method therefor, a crystalline composition thereof, and a pharmaceutical composition thereof, as well as the use of the crystalline for treating diseases associated with inhibition of growth factor receptor (for example c-Met) protein tyrosine kinase activity.

BACKGROUND OF THE INVENTION

The kinase, c-Met, is the prototypic member of a subfamily of heterodimeric receptor tyrosine kinases (RTKs) which include Met, Ron and Sea. The antiangiogenic and antiproliferative activity of c-Met becomes a attractive target. The endogenous ligand for c-Met is hepatocyte growth factor (HGF), also known as scatter factor (SF), because of its ability to disrupt colony formation in vitro. HGF is a derived cytokine known to induce activation of the receptor via autophosphorylation resulting in an increase of receptor dependent signaling in normal and neoplastic cells (Sonnenberg et al., J. Cell Biol., 123: 223-235, 1993; Matsumato et al., Crit. Rev. Oncog., 3: 27-54, 1992; Stoker et al., Nature, 327: 239-242, 1987). Anti-HGF antibodies or HGF antagonists also have been shown the inhibition of tumor metastasis.

WO2012034055 discloses N-(4-((7-((1-(cyclopentylamino)cyclopropyl)methoxy)-6-methoxyquinolin-4-yl)oxy)-3-fluorophenyl)-N-(4-fluorophenyl)cyclopropane-1,1-dicarboxamide as a c-Met kinase inhibitor (hereinafter referred to as the compound of formula I) and its preparation methods,

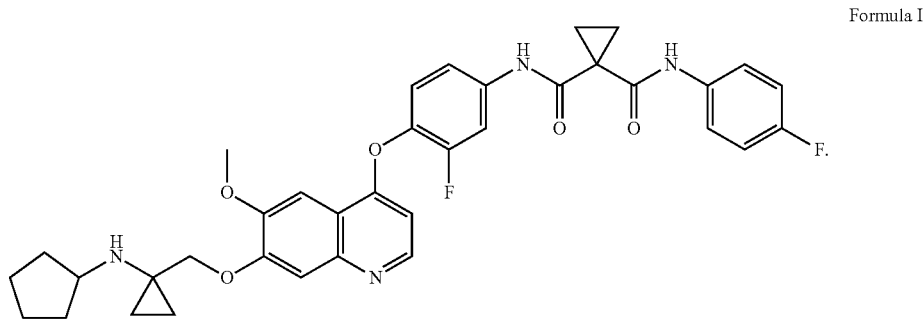 [SMILES: COc1cc2c(Oc3ccc(NC(=O)C4(C(=O)Nc5ccc(F)cc5)CC4)cc3F)ccnc2cc1OCC1(NC2CCCC2)CC1]

Formula I

It is generally expected that drugs have excellent properties in the following aspects: pharmacokinetics, bioavailability, hygroscopicity, stability, solubility, purity, ease of preparation, etc., to meet the needs of drugs in production, storage and formulation, etc. There is currently a need to provide compound of formula I with improved properties.

SUMMARY OF THE INVENTION

In one aspect, the present application provides crystalline form A of the compound of formula I,

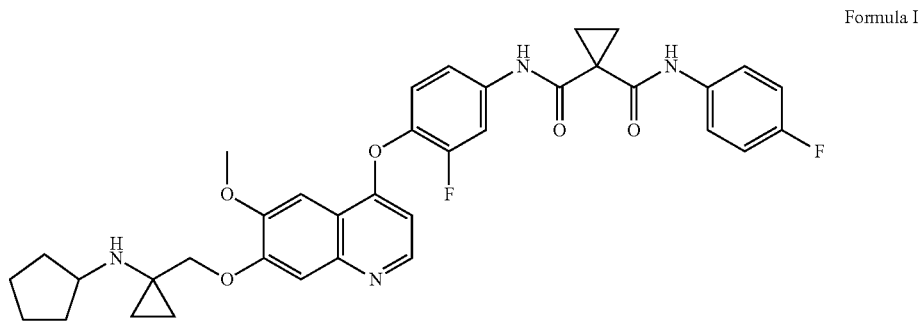 [SMILES: COc1cc2c(Oc3ccc(NC(=O)C4(C(=O)Nc5ccc(F)cc5)CC4)cc3F)ccnc2cc1OCC1(NC2CCCC2)CC1]

Formula I and in an X-ray powder diffraction pattern of crystalline form A with Cu Kα radiation thereof, diffraction peaks are present at 2θ angles of about 13.38, 15.71, 16.47, 20.15, 20.86, and 21.43 degrees.

In another aspect, the present application provides crystalline form B of the compound of formula I, and in an X-ray powder diffraction pattern of crystalline form B with Cu Kα radiation thereof, diffraction peaks are present at 2θ angles of about 7.44, 8.93, 10.44, and 17.84 degrees.

In another aspect, the present application provides crystalline form C of the compound of formula I, and in an X-ray powder diffraction pattern of crystalline form C with Cu Kα radiation thereof, diffraction peaks are present at 2θ angles of about 7.38, 10.33 and 17.84 degrees.

In another aspect, the present application provides crystalline form D of the compound of formula I, and in an X-ray powder diffraction pattern of crystalline form D with Cu Kα radiation thereof, diffraction peaks are present at 2θ angles of about 7.44, 13.38, 16.43, 20.14, 20.88 and 21.45 degrees.

In another aspect, the present application provides crystalline form E of the compound of formula I, and in an X-ray powder diffraction pattern of crystalline 1 form E with Cu Kα radiation thereof, diffraction peaks are present at 2θ angles of about 4.51, 6.64 and 10.66 degrees.

In still another aspect, the present application provides a crystalline composition comprising a crystalline of the compound of formula I, wherein the crystalline of the compound of formula I accounts for more than 50% by weight of the crystalline composition, preferably more than 80%, more preferably more than 90%, or most preferably more than 95%, and the crystalline of the compound of formula I is crystalline form A of the compound of formula I, crystalline form B of the compound of formula I, crystalline form C of the compound of formula I, crystalline form D of the compound of formula I or crystalline form E of the compound of formula I, or mixtures thereof.

In still another aspect, the present application provides a pharmaceutical composition comprising a therapeutically effective amount of a crystalline of the compound of formula I or the above-mentioned crystalline composition, wherein the crystalline of the compound of formula I is crystalline form A of the compound of formula I, crystalline form B of the compound of formula I, crystalline form C of the compound of formula I, crystalline form D of the compound of formula I or crystalline form E of the compound of formula I, or mixtures thereof.

In still another aspect, the present application provides a use of a crystalline of the compound of formula I or the above-mentioned crystalline composition or the above-mentioned pharmaceutical composition in the manufacture of a medicament for treating and/or preventing of diseases mediated by c-Met kinase, wherein the crystalline of the compound of formula I is crystalline form A of the compound of formula I, crystalline form B of the compound of formula I, crystal form C of the compound of formula I, crystal form D of the compound of formula I or crystalline form E of the compound of formula I, or mixtures thereof.

In another aspect, the present application provides a method for treating diseases mediated by c-Met kinase, comprising administering to a mammal in need of such treatment, preferably a human, a therapeutically effective amount of a crystalline of the compound of formula I or the above-mentioned crystalline composition or the above-mentioned pharmaceutical composition, wherein the crystalline of the compound of formula I is crystalline form A of the compound of formula I, crystalline form B of the compound of formula I, crystalline form C of the compound of formula I, crystalline form D of the compound of formula I or crystalline form E of the compound of formula I, or mixtures thereof.

In still another aspect, the present application provides a crystalline of the compound of formula I or the above-mentioned crystalline composition or the above-mentioned pharmaceutical composition for preventing and/or treating diseases mediated by c-Met kinase, wherein the crystalline of the compound of formula I is crystalline form A of the compound of formula I, crystalline form B of the compound of formula I, crystalline form C of the compound of formula I, crystalline form D of the compound of formula I or crystalline form E of the compound of formula I, or mixtures thereof.

DETAILED DESCRIPTION OF THE INVENTION

Figure 1:
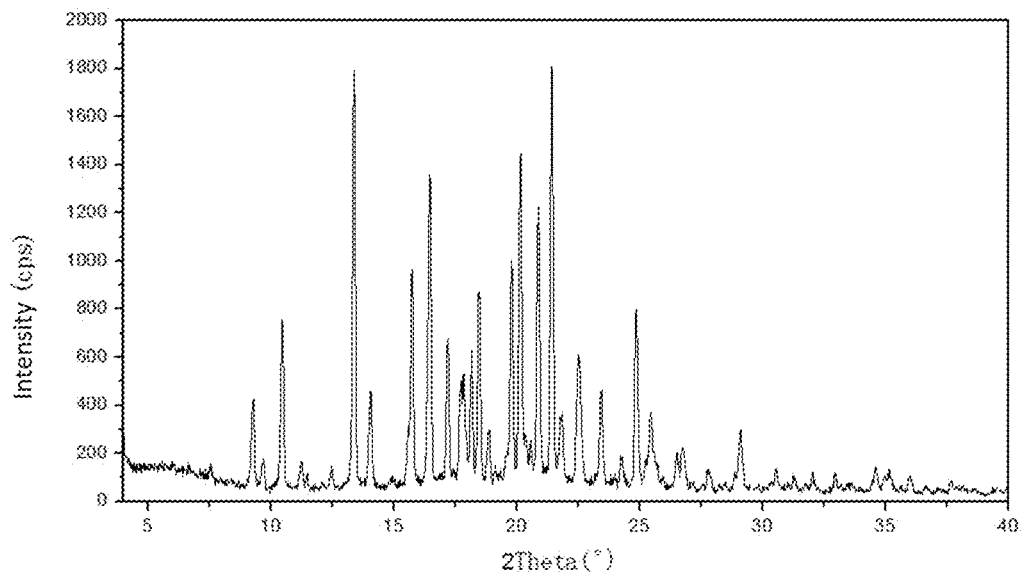
FIG. 1 is an XRPD pattern of crystalline form A of the compound of formula I prepared in Example 1.

This application provides a crystalline of N-(4-((7-((1-(cyclopentylamino)cyclopropyl)methoxy)-6-methoxyquinolin-4-yl)oxy)-3-fluorophenyl)-N-(4-fluorophenyl)cyclopropane-1,1-dicarboxamide (hereinafter referred to as a crystalline of the compound of formula I), which has excellent properties in at least one of pharmacokinetics, bioavailability, hygroscopicity, stability, solubility, purity, ease of preparation, etc.

According to specific embodiments of the present application, the crystalline of the compound of formula I provided herein include crystalline form A of N-(4-((7-((1-

(cyclopentylamino)cyclopropyl)methoxy)-6-methoxyquinolin-4-yl)oxy)-3-fluorophenyl)-N-(4-fluorophenyl)cyclopropane-1,1-dicarboxamide (hereinafter referred to as crystalline form A of the compound of formula I), crystalline form B of N-(4-((7-((1-(cyclopentylamino) cyclopropyl)methoxy)-6-methoxyquinolin-4-yl)oxy)-3-fluorophenyl)-N-(4-fluorophenyl)cyclopropane-1,1-dicarboxamide (hereinafter referred to as crystalline form B of the compound of formula I), crystalline form C of N-(4-((7-((1-(cyclopentylamino)cyclopropyl)methoxy)-6-methoxy-quinolin-4-yl)oxy)-3-fluorophenyl)-N-(4-fluorophenyl)cyclopropane-1,1-dicarboxamide (hereinafter referred to as crystalline form C of the compound of formula I), crystalline form D of N-(4-((7-((1-(cyclopentylamino)cyclopropyl)methoxy)-6-methoxyquinolin-4-yl)oxy)-3-fluorophenyl)-N-(4-fluorophenyl)cyclopropane-1,1-dicarboxamide (hereinafter referred to as crystalline form D of the compound of formula I), crystalline form E of N-(4-((7-((1-(cyclopentylamino)cyclopropyl)methoxy)-6-methoxyquinolin-4-yl)oxy)-3-fluorophenyl)-N-(4-fluorophenyl)cyclopropane-1,1-dicarboxamide (hereinafter referred to as crystalline form E of the compound of formula I).

In one aspect, the present application provides crystalline form A of the compound of formula I, and in an X-ray powder diffraction (XRPD) pattern with Cu Kα radiation thereof, diffraction peaks are present at 2θ angles of about 13.38, 15.71, 16.47, 20.15, 20.86 and 21.43 degrees, preferably diffraction peaks present at about 9.25, 10.45, 13.38, 14.03, 15.71, 16.47, 17.20, 17.85, 18.16, 18.48, 19.80, 20.15, 20.86, 21.43, 22.53, 23.43 and 24.87 degrees, more preferably diffraction peaks present at about 9.25, 10.45, 12.48, 13.38, 14.03, 15.71, 16.47, 17.20, 17.85, 18.16, 18.48, 18.85, 19.80, 20.15, 20.86, 21.43, 21.79, 22.53, 23.43, 24.87, 25.47 and 29.07 degrees, and most preferably diffraction peaks present at about 9.25, 9.64, 10.45, 11.27, 12.48, 13.38, 14.03, 15.71, 16.47, 17.20, 17.85, 18.16, 18.48, 18.85, 19.80, 20.15, 20.86, 21.43, 21.79, 22.53, 23.43, 24.25, 24.87, 25.47, 26.54, 26.76, 27.78, 29.07, 30.51, 31.99, 33.01, 34.65, 35.10 and 36.00 degrees.

Further, in the powder X-ray diffraction pattern of crystalline form A of the compound of formula I with Cu Kα radiation in the present application, the peak positions and relative intensities of the diffraction peaks are shown in Table 1 below:

TABLE 1

Peak Positions and Relative Intensities of Diffraction Peaks of X-ray Powder Diffraction Pattern of Crystalline Form A

| No. | 2θ (degree) | Relative Intensity (I/I$_0$) |
| --- | --- | --- |
| 1 | 9.25 | 19.1 |
| 2 | 9.64 | 5.6 |
| 3 | 10.45 | 40.2 |
| 4 | 11.27 | 6.1 |
| 5 | 12.48 | 4.5 |
| 6 | 13.38 | 100 |
| 7 | 14.03 | 23.1 |
| 8 | 15.71 | 50.6 |
| 9 | 16.47 | 73.9 |
| 10 | 17.20 | 34.2 |
| 11 | 17.85 | 25.4 |
| 12 | 18.16 | 29.7 |
| 13 | 18.48 | 45.3 |
| 14 | 18.85 | 12.1 |
| 15 | 19.80 | 53.4 |
| 16 | 20.15 | 76.8 |
| 17 | 20.86 | 65.1 |
| 18 | 21.43 | 99.9 |
| 19 | 21.79 | 15.0 |

TABLE 1-continued

Peak Positions and Relative Intensities of Diffraction Peaks of X-ray Powder Diffraction Pattern of Crystalline Form A

| No. | 2θ (degree) | Relative Intensity (I/I$_0$) |
| --- | --- | --- |
| 20 | 22.53 | 29.9 |
| 21 | 23.43 | 21.4 |
| 22 | 24.25 | 6.0 |
| 23 | 24.87 | 42.5 |
| 24 | 25.47 | 16.7 |
| 25 | 26.54 | 9.5 |
| 26 | 26.76 | 11.2 |
| 27 | 27.78 | 4.7 |
| 28 | 29.07 | 12.1 |
| 29 | 30.51 | 4.4 |
| 30 | 31.99 | 2.3 |
| 31 | 33.01 | 2.5 |
| 32 | 34.65 | 4.6 |
| 33 | 35.10 | 3.9 |
| 34 | 36.00 | 3.9 |

In a specific embodiment, the XRPD pattern of crystalline form A of the compound of formula I in the present application is shown in FIG. 1.

Figure 2:
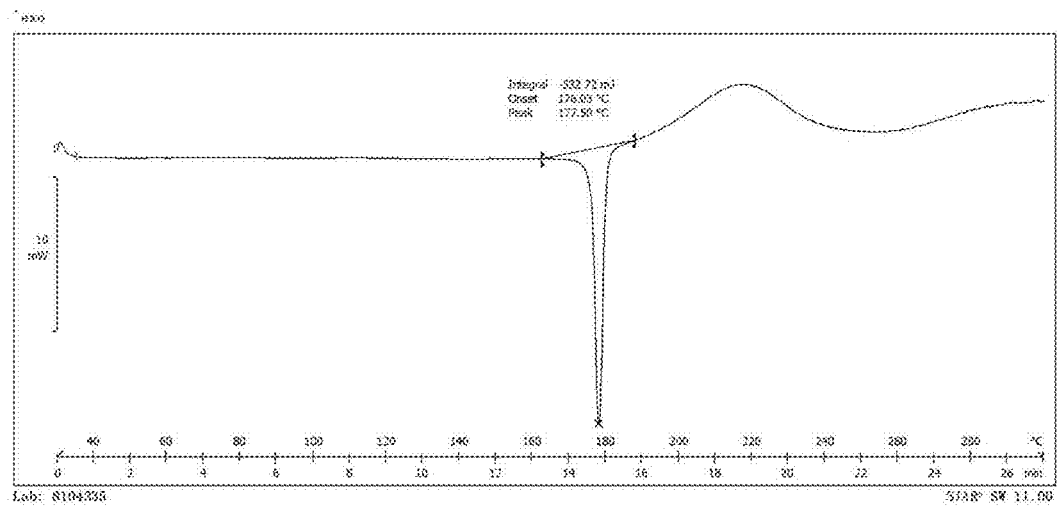
FIG. 2 is a DSC pattern of crystalline form A of the compound of formula I prepared in Example 1.

Without limitation, the differential scanning calorimetry (DSC) of crystalline form A of the compound of formula I in the present application has an endothermic peak at about 177.50° C., and specifically, the differential scanning calorimetry (DSC) pattern of crystalline form A of the compound of formula I is shown in FIG. 2.

Figure 3:
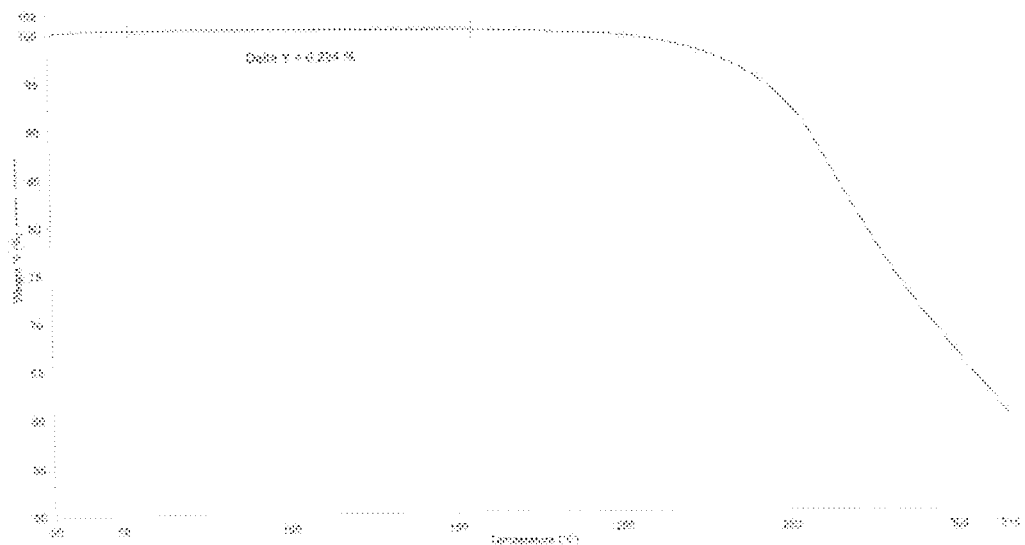
FIG. 3 is a thermogravimetric analysis (TGA) pattern of crystalline form A of the compound of formula I prepared in Example 1.

Without limitation, the thermogravimetric analysis (TGA) pattern of crystalline form A of the compound of formula I in the present application is shown in FIG. 3.

In another aspect, the present application provides crystalline form B of the compound of formula I, and in an X-ray powder diffraction pattern with Cu Kα radiation thereof, diffraction peaks are present at 2θ angles of about 7.44, 8.93, 10.44, and 17.84 degrees, preferably diffraction peaks present at about 7.44, 8.93, 10.26, 10.44, 10.70, 11.17, 12.65, 12.96, 14.35, 15.49, 16.34, 17.84, 18.28, 18.73, 20.96, 21.88, 22.42, 23.03, 24.17, 25.27 and 26.16 degrees, and most preferably diffraction peaks present at about 7.44, 8.93, 9.48, 10.26, 10.44, 10.70, 11.17, 11.85, 12.65, 12.96, 13.57, 14.35, 15.49, 15.75, 16.34, 17.84, 18.28, 18.73, 19.43, 20.02, 20.65, 20.96, 21.88, 22.42, 23.03, 24.17, 25.27, 25.99, 26.16 and 29.24 degrees.

Further, in the powder X-ray diffraction pattern of crystalline form B of the compound of formula I with Cu Kα radiation in the present application, the peak positions and relative intensities of the diffraction peaks are shown in Table 2 below:

TABLE 2

Peak Positions and Relative Intensities of Diffraction Peaks of X-ray Powder Diffraction Pattern of Crystalline Form B

| No. | 2θ (degree) | Relative Intensity (I/I$_0$) |
| --- | --- | --- |
| 1 | 7.44 | 100.0 |
| 2 | 8.93 | 26.6 |
| 3 | 9.48 | 3.0 |
| 4 | 10.26 | 22.8 |
| 5 | 10.44 | 31.0 |
| 6 | 10.70 | 17.3 |
| 7 | 11.17 | 8.4 |
| 8 | 11.85 | 3.9 |
| 9 | 12.65 | 5.8 |
| 10 | 12.96 | 18.6 |
| 11 | 13.57 | 5.0 |
| 12 | 14.35 | 13.5 |

TABLE 2-continued

Peak Positions and Relative Intensities of Diffraction Peaks
of X-ray Powder Diffraction Pattern of Crystalline Form B

| No. | 2θ (degree) | Relative Intensity (I/I₀) |
|---|---|---|
| 13 | 15.49 | 8.7 |
| 14 | 15.75 | 3.9 |
| 15 | 16.34 | 21.8 |
| 16 | 17.84 | 49.2 |
| 17 | 18.28 | 17.4 |
| 18 | 18.73 | 19.4 |
| 19 | 19.43 | 5.3 |
| 20 | 20.02 | 5.0 |
| 21 | 20.65 | 4.5 |
| 22 | 20.96 | 12.8 |
| 23 | 21.88 | 163 |
| 24 | 22.42 | 7.7 |
| 25 | 23.03 | 11.9 |
| 26 | 24.17 | 6.9 |
| 27 | 25.27 | 8.8 |
| 28 | 25.99 | 6.8 |
| 29 | 26.16 | 10.8 |
| 30 | 29.24 | 5.9 |

Figure 4:
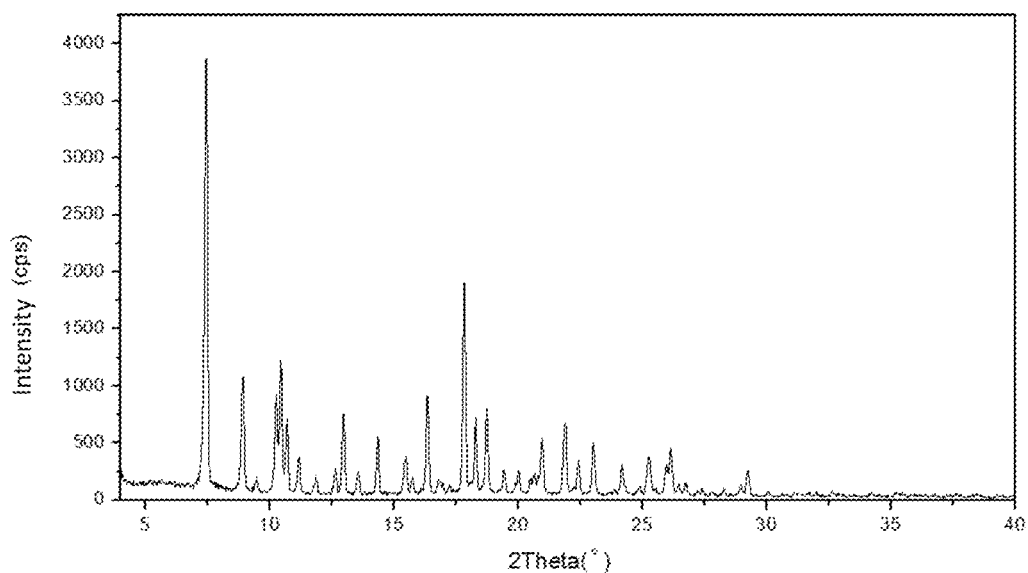
FIG. 4 is an XRPD pattern of crystalline form B of the compound of formula I prepared in Example 2.

In a specific embodiment, the XRPD pattern of crystalline form B of the compound of formula I in the present application is shown in FIG. 4.

Figures 5, 6:
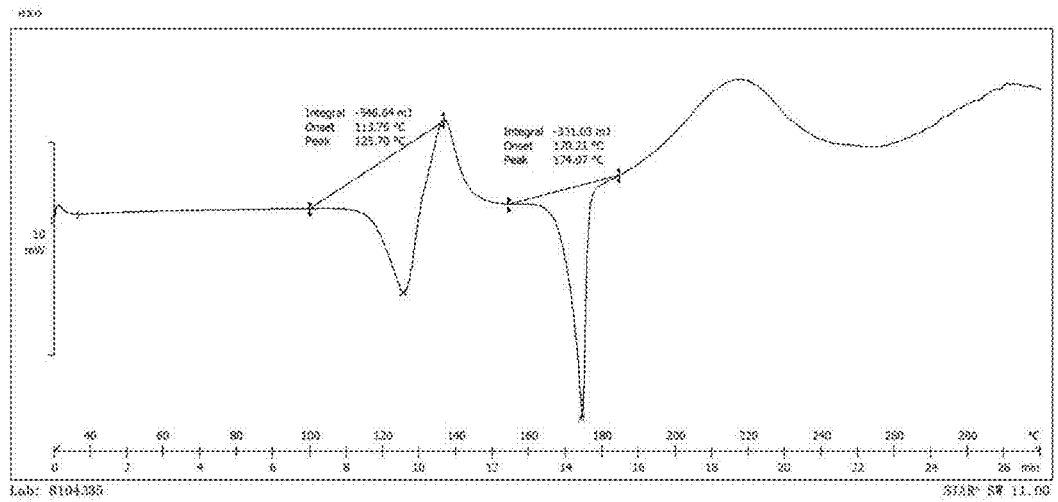
FIG. 5 is a DSC pattern of crystalline form B of the compound of formula I prepared in Example 2.
FIG. 6 is a thermogravimetric analysis (TGA) pattern of crystalline form B of the compound of formula I prepared in Example 2.

Without limitation, the differential scanning calorimetry (DSC) of crystalline form B of the compound of formula I in the present application has endothermic peaks at about 125.70° C. and 174.07° C., and specifically, the differential scanning calorimetry (DSC) pattern of crystalline form B of the compound of formula I is shown in FIG. 5.

Without limitation, the thermogravimetric analysis (TGA) pattern of crystalline form B of the compound of formula I in the present application is shown in FIG. 6.

In another aspect, the present application provides crystalline form C of the compound of formula I, and in an X-ray powder diffraction pattern with Cu Kα radiation thereof, diffraction peaks are present at 2θ angles of about 7.38, 10.33 and 17.84 degrees, preferably diffraction peaks present at about 7.38, 8.80, 10.33, 11.15, 15.30, 17.84, 18.18, 19.76, 21.03 and 21.86 degrees, and most preferably diffraction peaks present at about 7.38, 8.80, 10.33, 11.15, 11.71, 12.33, 12.58, 12.88, 13.50, 14.28, 15.30, 16.04, 16.33, 16.55, 17.84, 18.18, 18.43, 19.76, 21.03, 21.86, 22.83, 25.34 and 25.86 degrees.

Further, in the powder X-ray diffraction pattern of crystalline form C of the compound of formula I with Cu Kα radiation in the present application, the peak positions and relative intensities of the diffraction peaks are shown in Table 3 below:

TABLE 3

Peak Positions and Relative Intensities of Diffraction Peaks
of X-ray Powder Diffraction Pattern of Crystalline Form C

| No. | 2θ (degree) | Relative Intensity (I/I₀) |
|---|---|---|
| 1 | 7.38 | 100 |
| 2 | 8.80 | 18.5 |
| 3 | 10.33 | 37.3 |
| 4 | 11.15 | 11.9 |
| 5 | 11.71 | 2.9 |
| 6 | 12.33 | 10.6 |
| 7 | 12.58 | 6.5 |
| 8 | 12.88 | 8.5 |
| 9 | 13.50 | 5.4 |
| 10 | 14.28 | 7.4 |
| 11 | 15.30 | 24.9 |

TABLE 3-continued

Peak Positions and Relative Intensities of Diffraction Peaks
of X-ray Powder Diffraction Pattern of Crystalline Form C

| No. | 2θ (degree) | Relative Intensity (I/I₀) |
|---|---|---|
| 12 | 16.04 | 7.5 |
| 13 | 16.33 | 6.9 |
| 14 | 16.55 | 7.8 |
| 15 | 17.84 | 34.1 |
| 16 | 18.18 | 19.7 |
| 17 | 18.43 | 9.0 |
| 18 | 19.76 | 15.3 |
| 19 | 21.03 | 16.2 |
| 20 | 21.86 | 22.5 |
| 21 | 22.83 | 2.8 |
| 22 | 25.34 | 5.3 |
| 23 | 25.86 | 4.6 |

Figure 7:
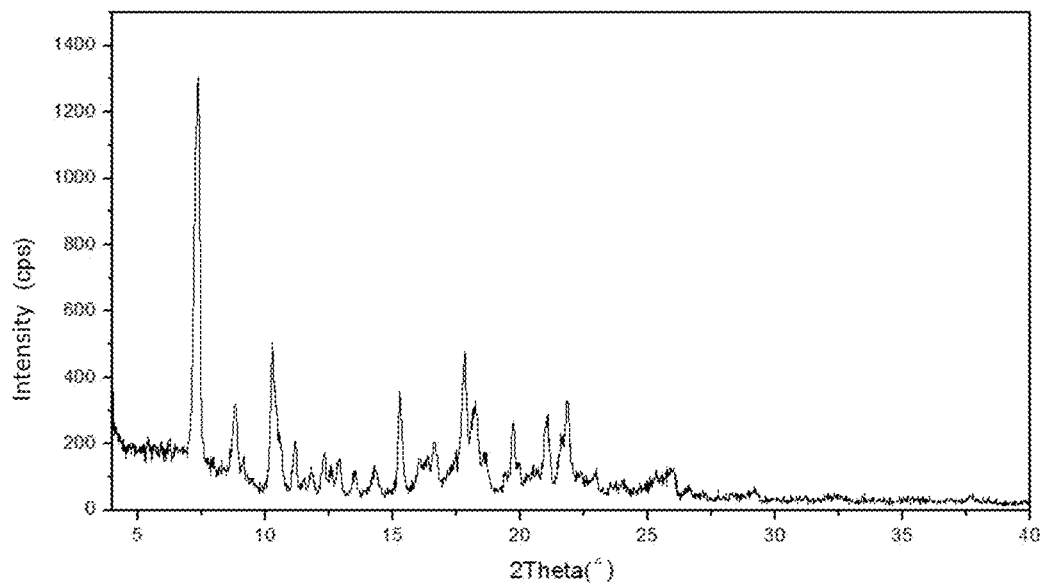
FIG. 7 is an XRPD pattern of crystalline form C of the compound of formula I prepared in Example 3.

In a specific embodiment, the XRPD pattern of crystalline form C of the compound of formula I in the present application is shown in FIG. 7.

In some embodiments of the present application, in the crystalline form C of the compound of formula I, the compound of formula I exists in a dioxane solvate form of the compound of formula I; specifically, in the dioxane solvate of the compound of formula I, the molar ratio of the compound of formula I to dioxane is 1-10:1, preferably 2-8:1, more preferably 2-3:1, and most preferably about 2.33:1.

Figure 8:
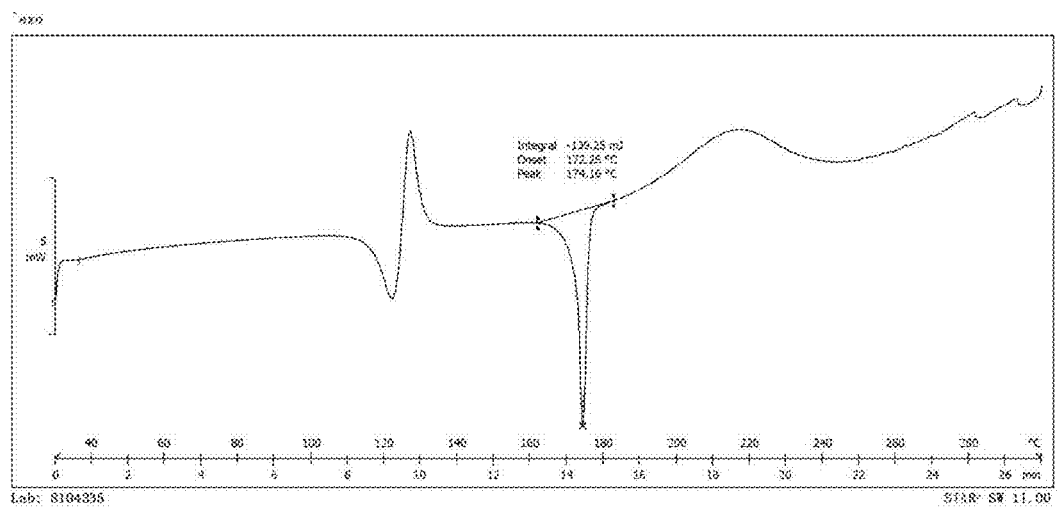
FIG. 8 is a DSC pattern of crystalline form C of the compound of formula I prepared in Example 3.

Without limitation, the differential scanning calorimetry (DSC) of crystalline form C of the compound of formula I in the present application has an endothermic peak at about 174.16° C., and specifically, the differential scanning calorimetry (DSC) pattern of crystalline form C of the compound of formula I is shown in FIG. 8.

Figure 9:
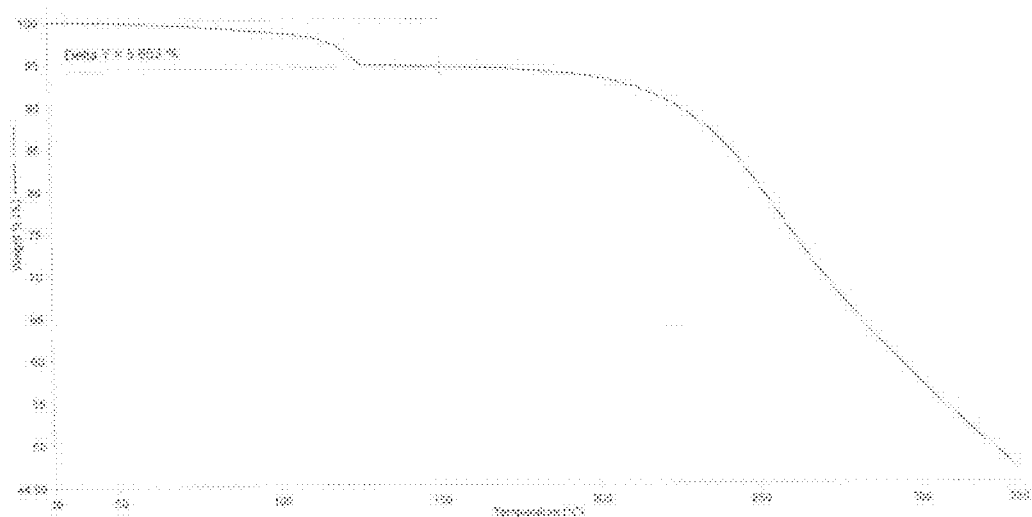
FIG. 9 is a thermogravimetric analysis (TGA) pattern of crystalline form C of the compound of formula I prepared in Example 3.

Without limitation, the thermogravimetric analysis (TGA) pattern of crystalline form C of the compound of formula I in the present application is shown in FIG. 9.

In still another aspect, the present application provides crystalline form D of the compound of formula I, and in an X-ray powder diffraction pattern with Cu Kα radiation thereof, diffraction peaks are present at 2θ angles of about 7.44, 13.38, 16.43, 20.14, 20.88 and 21.45 degrees, preferably diffraction peaks present at about 7.07, 7.44, 8.92, 9.23, 10.46, 13.38, 14.06, 15.76, 16.43, 17.21, 17.84, 18.17, 18.47, 19.82, 20.14, 20.88, 21.45, 21.82, 22.49, 23.44, 24.87, 25.44 and 29.09 degrees, and most preferably diffraction peaks present at about 7.07, 7.44, 8.05, 8.92, 9.23, 9.64, 10.46, 11.24, 12.63, 13.38, 14.06, 15.76, 16.43, 17.21, 17.84, 18.17, 18.47, 18.77, 19.82, 20.14, 20.88, 21.45, 21.82, 22.49, 23.44, 24.26, 24.87, 25.44, 26.06, 26.48, 26.80, 29.09, 33.00, 34.64 and 36.02 degrees.

Further, in the powder X-ray diffraction pattern of crystalline form D of the compound of formula I with Cu Kα radiation in the present application, the peak positions and relative intensities of the diffraction peaks are shown in Table 4 below:

TABLE 4

Peak Positions and Relative Intensities of Diffraction Peaks
of X-ray Powder Diffraction Pattern of Crystalline Form D

| No. | 2θ (degree) | Relative Intensity (I/I₀) |
|---|---|---|
| 1 | 7.07 | 26.0 |
| 2 | 7.44 | 61.7 |
| 3 | 8.05 | 5.8 |
| 4 | 8.92 | 11.9 |

TABLE 4-continued

Peak Positions and Relative Intensities of Diffraction Peaks
of X-ray Powder Diffraction Pattern of Crystalline Form D

| No. | 2θ (degree) | Relative Intensity (I/I$_0$) |
|---|---|---|
| 5 | 9.23 | 12.6 |
| 6 | 9.64 | 8.5 |
| 7 | 10.46 | 40.4 |
| 8 | 11.24 | 11.3 |
| 9 | 12.63 | 5.6 |
| 10 | 13.38 | 84.4 |
| 11 | 14.06 | 16.6 |
| 12 | 15.76 | 29.2 |
| 13 | 16.43 | 49.4 |
| 14 | 17.21 | 36.2 |
| 15 | 17.84 | 39.7 |
| 16 | 18.17 | 27.8 |
| 17 | 18.47 | 35.0 |
| 18 | 18.77 | 8.5 |
| 19 | 19.82 | 32.7 |
| 20 | 20.14 | 83.9 |
| 21 | 20.88 | 68.5 |
| 22 | 21.45 | 100.0 |
| 23 | 21.82 | 19.6 |
| 24 | 22.49 | 26.7 |
| 25 | 23.44 | 22.1 |
| 26 | 24.26 | 8.0 |
| 27 | 24.87 | 46.0 |
| 28 | 25.44 | 15.7 |
| 29 | 26.06 | 6.0 |
| 30 | 26.48 | 7.5 |
| 31 | 26.80 | 7.1 |
| 32 | 29.09 | 24.0 |
| 33 | 33.00 | 4.3 |
| 34 | 34.64 | 5.7 |
| 35 | 36.02 | 4.5 |

Figure 10:
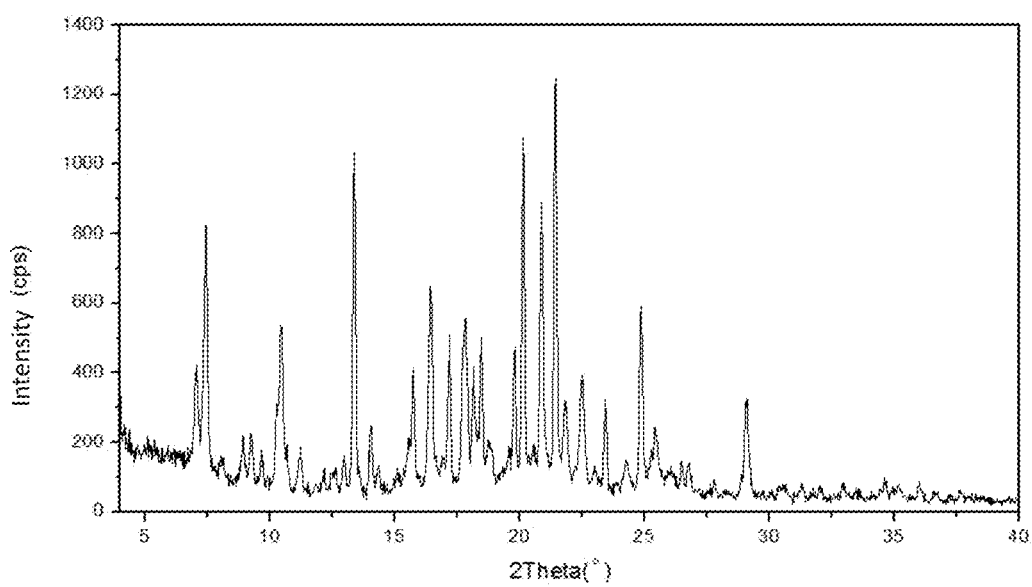
FIG. 10 is an XRPD pattern of crystalline form D of the compound of formula I prepared in Example 4.

In a specific embodiment, the XRPD pattern of crystalline form D of the compound of formula I in the present application is shown in FIG. 10.

Figure 11:
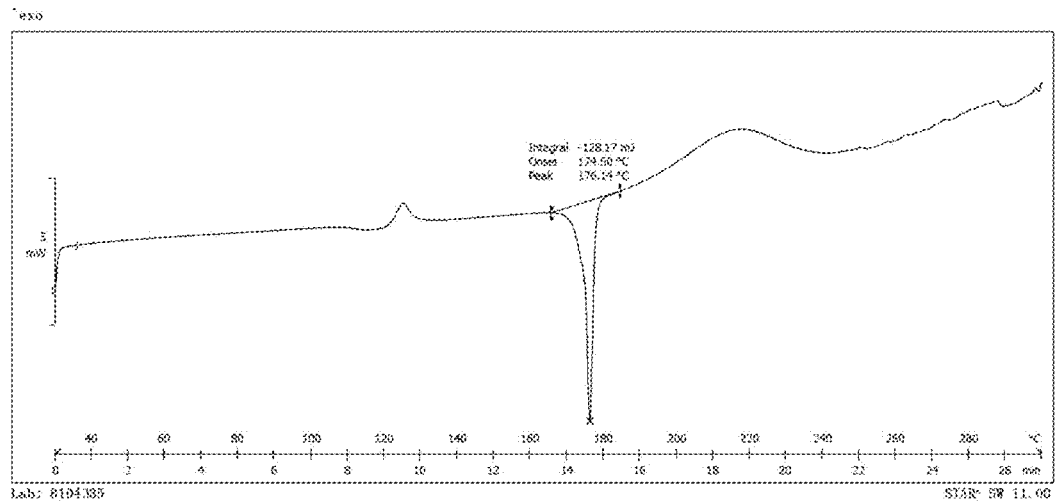
FIG. 11 is a DSC pattern of crystalline form D of the compound of formula I prepared in Example 4.

Without limitation, the differential scanning calorimetry (DSC) of crystalline form D of the compound of formula I in the present application has an endothermic peak at about 176.14° C., and specifically, the differential scanning calorimetry (DSC) pattern of crystalline form D of the compound of formula I is shown in FIG. 11.

Figure 12:
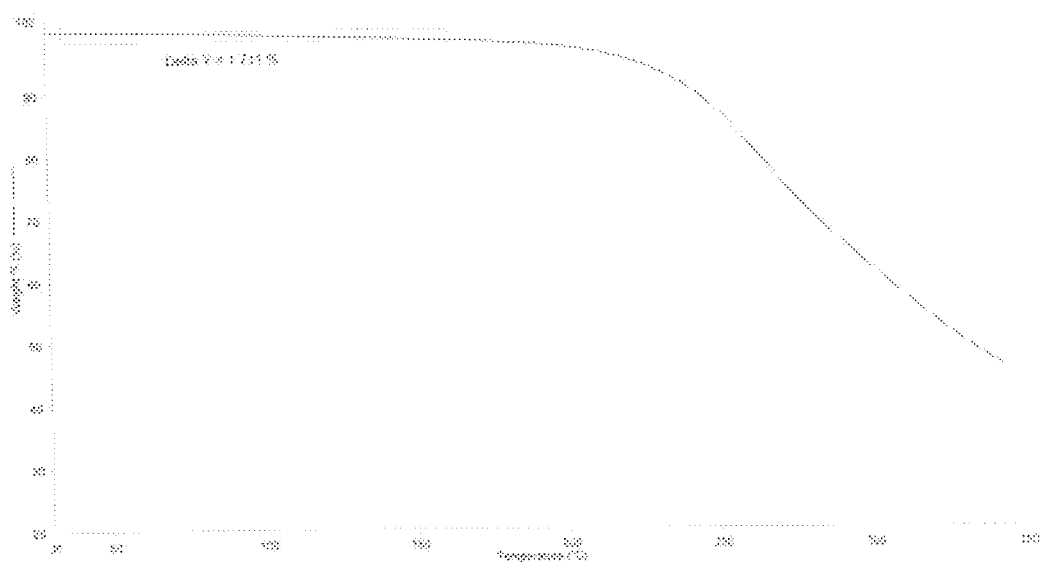
FIG. 12 is a thermogravimetric analysis (TGA) pattern of crystalline form D of the compound of formula I prepared in Example 4.

Without limitation, the thermogravimetric analysis (TGA) pattern of crystalline form D of the compound of formula I in the present application is shown in FIG. 12.

In still another aspect, the present application provides crystalline form E of the compound of formula I, and in an X-ray powder diffraction pattern with Cu Kα radiation thereof, diffraction peaks are present at 2θ angles of about 4.51, 6.64 and 10.66 degrees, preferably diffraction peaks present at about 4.51, 6.64, 9.03, 9.64, 10.66, 16.69 and 17.12 degrees, more preferably diffraction peaks present at about 4.51, 6.64, 9.03, 9.64, 10.66, 13.26, 13.59, 15.20, 15.85, 16.69, 17.12, 19.33, 20.49, 22.12, and 22.50 degrees, and most preferably diffraction peaks present at about 4.51, 6.64, 9.03, 9.64, 10.66, 13.26, 13.59, 14.40, 15.20, 15.85, 16.69, 17.12, 17.36, 18.10, 19.33, 20.49, 21.38, 22.12, and 22.50 degrees.

Further, in the powder X-ray diffraction pattern of crystalline form E of the compound of formula I with Cu Kα radiation in the present application, the peak positions and relative intensities of the diffraction peaks are shown in Table 5 below:

TABLE 5

Peak Positions and Relative Intensities of Diffraction Peaks
of X-ray Powder Diffraction Pattern of Crystalline Form E

| No. | 2θ (degree) | Relative Intensity (I/I$_0$) |
|---|---|---|
| 1 | 4.51 | 55.6 |
| 2 | 6.64 | 68.8 |
| 3 | 9.03 | 48.7 |
| 4 | 9.64 | 44.7 |
| 5 | 10.66 | 100.0 |
| 6 | 13.26 | 25.3 |
| 7 | 13.59 | 19.6 |
| 8 | 14.40 | 9.3 |
| 9 | 15.20 | 12.1 |
| 10 | 15.85 | 15.8 |
| 11 | 16.69 | 53.9 |
| 12 | 17.12 | 44.9 |
| 13 | 17.36 | 17.6 |
| 14 | 18.10 | 9.4 |
| 15 | 19.33 | 12.2 |
| 16 | 20.49 | 12.1 |
| 17 | 21.38 | 8.7 |
| 18 | 22.12 | 24.7 |
| 19 | 22.50 | 16.2 |

Figure 13:
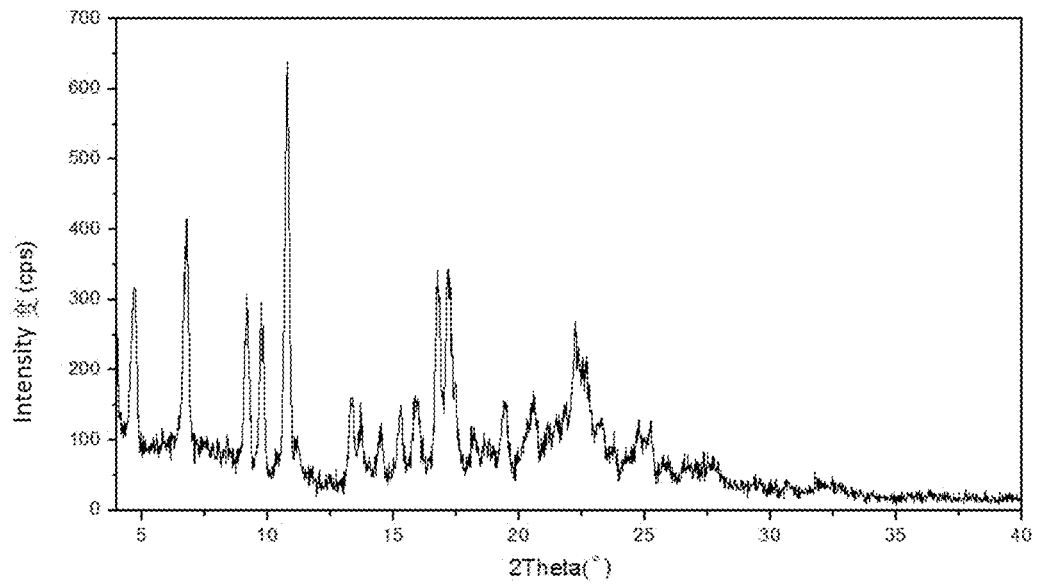
FIG. 13 is an XRPD pattern of crystalline form E of the compound of formula I prepared in Example 5.

In a specific embodiment, the XRPD pattern of crystalline form E of the compound of formula I in the present application is shown in FIG. 13.

Figure 14:
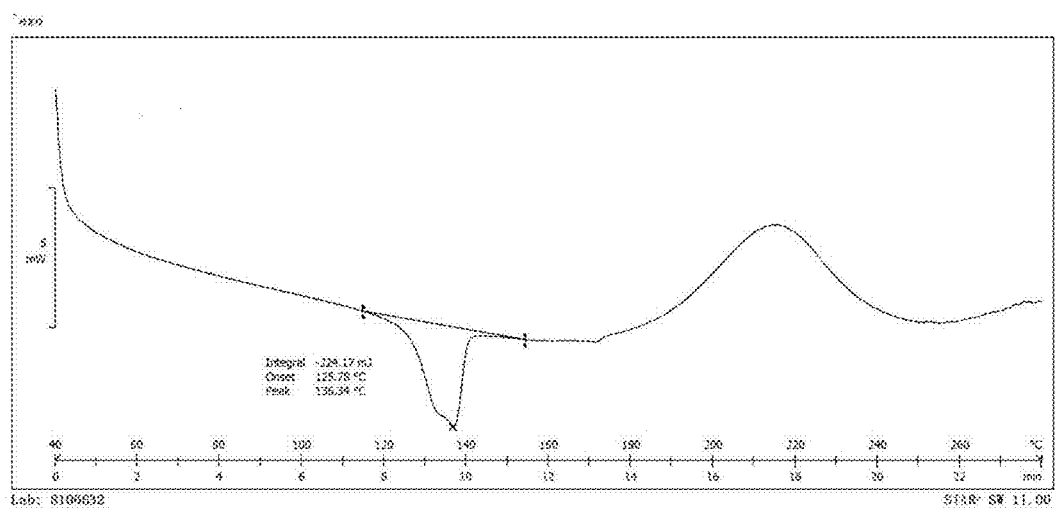
FIG. 14 is a DSC pattern of crystalline form E of the compound of formula I prepared in Example 5.

Without limitation, the differential scanning calorimetry (DSC) of crystalline form E of the compound of formula I in the present application has an endothermic peak at about 136.34° C., and specifically, the differential scanning calorimetry (DSC) pattern of crystalline form E of the compound of formula I is shown in FIG. 14.

Figure 15:
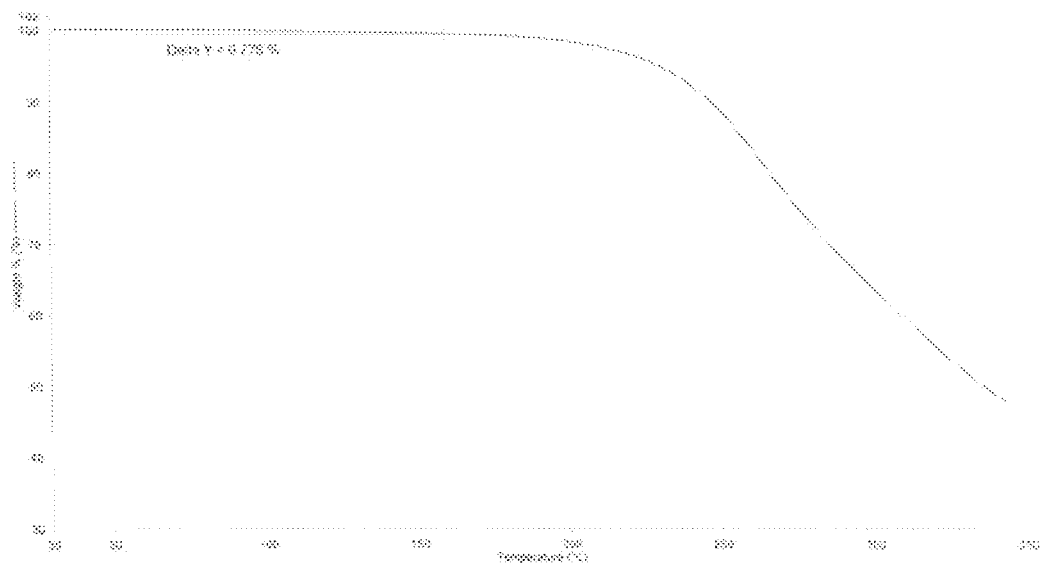
FIG. 15 is a thermogravimetric analysis (TGA) pattern of crystalline form E of the compound of formula I prepared in Example 5.

Without limitation, the thermogravimetric analysis (TGA) pattern of crystalline form E of the compound of formula I in the present application is shown in FIG. 15.

In the present application, the instrument model for X-ray powder diffraction spectrometry is Bruker D2 X-ray diffractometer. Conditions and methods: 30 kv 10 mA, slit: 0.6/3/Ni/8, 2theta: 4-40°, time [s]: 0.1, step: 0.02°.

In the present application, the instrument model for DSC spectrometry is METTLER TOLEDO DSC1. Conditions and methods: temperature is increased by 10° C./min in a range of 30-300° C.

In the present application, the instrument model for TGA spectrometry is PerKinElmerPyris 1 thermogravimetric analyzer. Conditions and methods: temperature is increased by 20° C./min in a range of 25-700° C.

For any given crystalline form, the relative intensity of the diffraction peak may vary due to preferred orientation caused by factors such as crystalline morphology, which is well known in the field of crystallography. Where there is an influence of preferred orientation, the peak intensity is varied, but the diffraction peak position of the crystalline cannot be varied. In addition, for any given crystalline form, there may be a slight error in the position of the peak, which is also well known in the field of crystallography. For example, due to temperature changes during sample analysis, sample movement, or instrument calibration, etc., the peak position may be shifted, and the measurement error of the 2θ value is sometimes about ±0.2 degrees. Therefore, it is well known to those skilled in the art that when determining each crystalline structure, this error should be taken into account.

DSC measures the transition temperature of a crystalline when it absorbs or releases heat due to changes in its crystalline structure or crystalline melting. For the same crystalline form of the same compound, in continuous analysis, the thermal transition temperature and melting point error are typically within about 5° C., usually within about 3° C. When we say that a compound has a given DSC peak or melting point, this means the DSC peak or melting point±5° C. DSC provides an auxiliary method to identify different crystalline forms. Different crystalline forms can be identified according to their different transition temperature characteristics. It should be noted that for mixtures, the DSC peak or melting point may vary in a larger range. In addition, due to the accompanying decomposition during the melting of substance, the melting temperature is related to the rate of temperature increase.

In another aspect, the present application provides a method for preparing crystalline form A of the compound of formula I, comprising the following steps of:

(1) mixing the compound of formula I and solvent A to obtain a solution of the compound of formula I; and (2) precipitating solid;

wherein the solvent A in step (1) is selected from toluene, butanone, acetonitrile, a mixed solvent of acetonitrile and water or ethyl acetate, preferably toluene.

In some embodiments of the present application, solvent A is selected from a mixed solvent of acetonitrile and water, wherein the volume fraction of acetonitrile in the mixed solvent is 65%-95%.

In some embodiments of the present application, the volume of solvent A is 1-50 mL, preferably 2-15 mL, based on 1 g of the compound of formula I.

In some embodiments of the present application, the volume of solvent A is 5 mL, based on 1 g of the compound of formula I.

In some embodiments of the present application, step (1) is performed at a temperature ranging from 0° C. to the boiling point of the solvent system after mixing, and preferably step (1) is performed at the boiling point temperature of the solvent system after mixing.

In some embodiments of the present application, a solid is precipitated under a state of standing, shaking or stirring in step (2), and preferably step (2) is performed under stirring. Step (2) can be performed at room temperature.

In some embodiments of the present application, the method for preparing crystalline form A further includes separating the solid precipitated in step (2), for example, separating by filtration. In some embodiments of the present application, it further includes drying the separated solid, and the drying temperature may be 60° C.

In yet another aspect, the present application provides a method for preparing crystalline form B of the compound of formula I, comprising the following steps of:

(1) mixing the compound of formula I and solvent B to obtain a solution of the compound of formula I; and (2) precipitating solid;

wherein the solvent B in step (1) is selected from methanol, ethanol, acetone, a mixed solvent of methanol and water, a mixed solvent of ethanol and water, a mixed solvent of acetone and water, or a mixed solvent of ethanol and butanone, preferably ethanol; wherein the volume fraction of methanol in the mixed solvent of methanol and water is 95%; wherein the volume fraction of ethanol in the mixed solvent of ethanol and water is 65%-95%; wherein the volume fraction of acetone in the mixed solvent of acetone and water is 65%-95%; wherein the volume fraction of butanone in the mixed solvent of ethanol and butanone is not more than 30%.

In some embodiments of the present application, the volume of solvent B is 1-50 mL, preferably 5-20 mL, based on 1 g of the compound of formula I.

In some specific embodiments of the present application, the volume of solvent B is 8.75 mL, based on 1 g of the compound of formula I.

In some embodiments of the present application, step (1) is performed at a temperature ranging from 0° C. to the boiling point of the solvent system after mixing, and preferably step (1) is performed at the boiling point temperature of the solvent system after mixing.

In some embodiments of the present application, a solid is precipitated under a state of standing, shaking or stirring in step (2), and preferably step (2) is performed under stirring. Step (2) can be performed at room temperature.

In some embodiments of the present application, the method for preparing crystalline form B further includes separating the solid precipitated in step (2), for example, separating by filtration. In some embodiments of the present application, it further includes drying the separated solid, and the drying temperature may be 60° C.; the drying may be performed under reduced pressure.

In still another aspect, the present application provides a method for preparing crystalline form C of the compound of formula I, comprising the following steps of:

(1) mixing the compound of formula I and solvent C to obtain a solution of the compound of formula I; and (2) precipitating solid;

wherein the solvent C in step (1) is dioxane.

In some embodiments of the present application, the volume of solvent C is 1-100 mL, preferably 5-20 mL, based on 1 g of the compound of formula I.

In some specific embodiments of the present application, the volume of solvent C is 7.5 mL, based on 1 g of the compound of formula I.

In some embodiments of the present application, step (1) is performed at a temperature ranging from 0° C. to the boiling point of the solvent system after mixing, and preferably step (1) is performed at the boiling point temperature of the solvent system after mixing.

In some embodiments of the present application, a solid is precipitated under a state of standing, shaking or stirring in step (2), and preferably step (2) is performed under stirring. Step (2) can be performed at room temperature.

In some embodiments of the present application, the method for preparing crystalline form C further includes separating the solid precipitated in step (2), for example, separating by filtration. In some embodiments of the present application, it further includes drying the separated solid, and the drying temperature may be 60° C.

In still another aspect, the present application provides a method for preparing crystalline form D of the compound of formula I, comprising the following steps of:

(1) mixing the compound of formula I and solvent D to obtain a solution of the compound of formula I; and (2) precipitating solid;

wherein the solvent D in step (1) is a mixed solvent of ethanol and water; wherein the volume fraction of ethanol in the mixed solvent of ethanol and water is 55%.

In some embodiments of the present application, the volume of solvent D is 1-50 mL, preferably 5-20 mL, based on 1 g of the compound of formula I.

In some specific embodiments of the present application, the volume of solvent D is 10 mL, based on 1 g of the compound of formula I.

In some embodiments of the present application, step (1) is performed at a temperature ranging from 0° C. to the boiling point of the solvent system after mixing, and preferably step (1) is performed at the boiling point temperature of the solvent system after mixing.

In some embodiments of the present application, a solid is precipitated under a state of standing, shaking or stirring in step (2), and preferably step (2) is performed under stirring. Step (2) can be performed at room temperature.

In some embodiments of the present application, the method for preparing crystalline form D further includes separating the solid precipitated in step (2), for example, separating by filtration. In some embodiments of the present application, it further includes drying the separated solid, and the drying temperature may be 45° C.; and the drying may be performed under reduced pressure.

In still another aspect, the present application provides a method for preparing crystalline form E of the compound of formula I, comprising the following steps of:

(1) mixing the compound of formula I and solvent E to obtain a solution of the compound of formula I; and (2) precipitating solid;

wherein the solvent E in step (1) is a mixed solvent of methanol and water; wherein the volume fraction of methanol in the mixed solvent of methanol and water is 75%-85%.

In some embodiments of the present application, the volume of solvent E is 1-50 mL, preferably 5-20 mL, based on 1 g of the compound of formula I.

In some specific embodiments of the present application, the volume of solvent E is 10 mL, based on 1 g of the compound of formula I.

In some embodiments of the present application, step (1) is performed at a temperature ranging from 0° C. to the boiling point of the solvent system after mixing, and preferably step (1) is performed at the boiling point temperature of the solvent system after mixing.

In some embodiments of the present application, a solid is precipitated under a state of standing, shaking or stirring in step (2), and preferably step (2) is performed under stirring. Step (2) can be performed at room temperature.

In some embodiments of the present application, the method for preparing crystalline form E further includes separating the solid precipitated in step (2), for example, separating by filtration. In some embodiments of the present application, it further includes drying the separated solid.

In yet another aspect, the present application provides a crystalline composition comprising a crystalline of the compound of formula I, wherein the crystalline of the compound of formula I accounts for more than 50% by weight of the crystalline composition, preferably more than 80%, more preferably more than 90%, and most preferably more than 95%, wherein the crystalline of the compound of formula I is crystalline form A of the compound of formula I, crystalline form B of the compound of formula I, crystalline form C of the compound of formula I, crystalline form D of the compound of formula I or crystalline form E of the compound of formula I, or mixtures of thereof.

In yet another aspect, the present application provides a pharmaceutical composition comprising a therapeutically effective amount of a crystalline of the compound of formula I described herein, or the above-mentioned crystalline composition, wherein the crystalline of the compound of formula I is crystalline form A of the compound of formula I, crystalline form B of the compound of formula I, crystalline form C of the compound of formula I, crystalline form D of the compound of formula I or crystalline form E of the compound of formula I, or mixtures thereof. The pharmaceutical composition of the present application may or may not contain pharmaceutically acceptable excipients. In addition, the pharmaceutical composition of the present application may further include one or more other therapeutic agents.

The "pharmaceutically acceptable excipients" refer to inert substances that are administered together with active ingredient and facilitate administration of the active ingredient, including but not limited to any acceptable glidants, sweeteners, diluents, preservatives, dyes/colorants, flavor enhancers, surfactants, lubricants, dispersants, disintegrants, suspending agents, stabilizers, isotonic agents, solvents or emulsifier licensed by the State Food and Drug Administration for use in humans or animals (e.g., livestock). Non-limiting examples of such excipients include calcium carbonate, calcium phosphate, various sugars and various types of starch, cellulose derivatives, gelatin, vegetable oil, and polyethylene glycol.

The pharmaceutical composition of the present application can be formulated into solid, semi-solid, liquid or gaseous formulations, such as tablets, pills, capsules, powders, granules, ointments, emulsions, suspensions, solutions, suppositories, injections, inhalants, gels, microspheres, aerosols, etc.

Typical routes for administering the pharmaceutical compositions of the present application include, but are not limited to oral, rectal, transmucosal, enteral, or topical, transdermal, inhalation, parenteral, sublingual, intravaginal, intranasal, intraocular, intraperitoneal, intramuscular, subcutaneous and intravenous administration. A preferred route of administration is oral administration.

In still another aspect, the present application provides a use of a crystalline of the compound of formula I, or the above-mentioned crystalline composition, or the above-mentioned pharmaceutical composition in the manufacture of a medicament for treating and/or preventing of diseases mediated by c-Met kinase, wherein the crystalline of the compound of formula I is crystalline form A of the compound of formula I, crystalline form B of the compound of formula I, crystalline form C of the compound of formula I, crystalline form D of the compound of formula I or crystalline form E of the compound of formula I, or mixtures of thereof.

In still another aspect, the present application provides a use of a crystalline of the compound of formula I, or the above-mentioned crystalline composition, or the above-mentioned pharmaceutical composition in treating and/or preventing of diseases mediated by c-Met kinase, wherein the crystalline of the compound of formula I is crystalline form A of the compound of formula I, crystalline form B of the compound of formula I, crystalline form C of the compound of formula I, crystalline form D of the compound of formula I or crystalline form E of the compound of formula I, or mixtures of thereof.

In still another aspect, the present application provides a method for treating diseases mediated by c-Met kinase, comprising administering to a mammal in need of such treatment, preferably humans, a therapeutically effective amount of a crystalline of the compound of formula I, or the above-mentioned crystalline composition, or the above-mentioned pharmaceutical composition, wherein the crystalline of the compound of formula I is crystalline form A of the compound of formula I, crystalline form B of the compound of formula I, crystalline form C of the compound of formula I, crystalline form D of the compound of formula I or crystalline form E of the compound of formula I, or mixtures thereof.

For drugs or pharmacologically active agents, the term "therapeutically effective amount" refers to a sufficient amount of a drug or medicament that is non-toxic but could achieve the desired effect. The determination of the effective amount varies from person to person, depending on the age and general condition of the recipient, and also on the specific active substances. The appropriate effective amount in a case can be determined by those skilled in the art based on routine experiments.

In still another aspect, the present application provides a crystalline of the compound of formula I, or the above-mentioned crystalline composition, or the above-mentioned pharmaceutical composition for preventing or treating diseases mediated by c-Met kinase, wherein the crystalline of the compound of formula I is crystalline form A of the compound of formula I, crystalline form B of the compound of formula I, crystalline form C of the compound of formula I, crystalline form D of the compound of formula I or crystalline form E of the compound of formula I, or mixtures thereof.

In some embodiments of the present application, the above-mentioned disease mediated by c-Met kinase is cancer, such as lung cancer.

The technical solution of the present application will be described in detail below in combination with drawings and examples, but the protecting scope of the present application includes but is not limited thereto. The compound of formula I is prepared by reference to the methods disclosed in WO2012034055.

Example 1 Preparation of Crystalline Form A of the Compound of Formula I 20 g of the compound of formula I was dissolved in toluene (100 mL), after refluxed and dissolved to clarification, filtered, and the filtrate was stirred at room temperature for crystallinelization, filtered, and air-blast dried at 60° C. under atmospheric pressure to give crystalline form A. The X-ray powder diffraction pattern using Cu Kα radiation is shown in FIG. 1, and the differential scanning calorimetry (DSC) pattern is shown in FIG. 2, and the thermogravimetric analysis (TGA) pattern is shown in FIG. 3.

Example 2 Preparation of Crystalline Form B of the Compound of Formula I 20 g of the compound of formula I was dissolved in ethanol (175 mL), after refluxed and dissolved to clarification, filtered, and the filtrate was stirred at room temperature for crystallinelization, filtered, and dried at 60° C. under reduced pressure to give crystalline form B. The X-ray powder diffraction pattern using Cu Kα radiation is shown in FIG. 4, and the differential scanning calorimetry (DSC) pattern is shown in FIG. 5, and the thermogravimetric analysis (TGA) pattern is shown in FIG. 6.

Example 3 Preparation of Crystalline Form C of the Compound of Formula I 20 g of the compound of formula I was dissolved in dioxane (150 mL), after refluxed and dissolved to clarification, filtered, and the filtrate was stirred at room temperature for crystallinelization, filtered, and air-blast dried at 60° C. under atmospheric pressure to give crystalline form C. The X-ray powder diffraction pattern using Cu Kα radiation is shown in FIG. 7, and the differential scanning calorimetry (DSC) pattern is shown in FIG. 8, and the thermogravimetric analysis (TGA) pattern is shown in FIG. 9.

Example 4 Preparation of Crystalline Form D of the Compound of Formula I 20 g of the compound of formula I was dissolved in 55% ethanol aqueous solution (200 mL), after refluxed until it was just dissolved to clarification, filtered, and the filtrate was stirred at room temperature for crystallinelization, filtered, and dried under reduced pressure at 45° C. to give crystalline form D. The X-ray powder diffraction pattern using Cu Kα radiation is shown in FIG. 10, and the differential scanning calorimetry (DSC) pattern is shown in FIG. 11, and the thermogravimetric analysis (TGA) pattern is shown in FIG. 12.

Example 5 Preparation of Crystalline Form E of the Compound of Formula I 20 g of the compound of formula I was dissolved in 85% methanol aqueous solution (200 mL), after refluxed and dissolved to clarification, filtered, and the filtrate was stirred at room temperature for crystallinelization, filtered, and allowed to stand at room temperature for 10 days to give crystalline form E. The X-ray powder diffraction pattern using Cu Kα radiation is shown in FIG. 13, and the differential scanning calorimetry (DSC) pattern is shown in FIG. 14, and the thermogravimetric analysis (TGA) pattern is shown in FIG. 15.

Example 6 Hygroscopicity Test

Took the crystalline form A, crystalline form B, crystalline form D and crystalline form E of the compound of formula I to conduct test according to the "Guidelines for Drug Moisture Test" of the Chinese Pharmacopoeia 2015 Edition Fourth General Chapter 9103, and respectively, the weight gain of samples due to hygroscopicity was calculated. The results are shown in Table 6.

TABLE 6

Results of Hygroscopicity Test

| Compound | Weight Gain due to Hygroscopicity (%) |
| --- | --- |
| Example 1 | Less than 0.2 |
| Example 2 | Less than 0.2 |
| Example 4 | Less than 0.2 |
| Example 5 | Less than 0.2 |

Example 7 Determination of Intrinsic Dissolution Rate

The crystalline form A, crystalline form B, crystalline form D and crystalline form E of the compound of formula I were each about 80 mg, and were directly compressed into tablets under high pressure (tablet core diameter 4 mm, pressure 150 kg, maintenance time 2 min, repeated three times). 700 mL of 0.01 mol/L hydrochloric acid solution was used as a medium, and the intrinsic dissolution rate of the drug substance was determined. The results are shown in Table 7.

TABLE 7

Intrinsic Dissolution Rate of Compound of Formula I

| Crystalline Form | Intrinsic Dissolution Rate | |
|---|---|---|
| | μg/ml/min | mg/min/cm² |
| Crystalline Form A of the Compound of Formula I | 2.18 | 12.15 |
| Crystalline Form B of the Compound of Formula I | 4.61 | 25.69 |
| Crystalline Form D of the Compound of Formula I | 7.04 | 39.24 |
| Crystalline Form E of the Compound of Formula I | 1.22 | 6.80 |

Example 8 Pharmacokinetic Test in Rats 1.1 Test Purpose

The relative bioavailability of the compound of formula I in vivo was evaluated, after SD rats were gavaged with crystalline form A, crystalline form B, crystalline form D and crystalline form E of the compound of formula I.

1.2 Test Materials

SD rats: Purchased from Shanghai Cipur Bikai Laboratory Animal Co., Ltd.

Test samples: crystalline form A, crystalline form B, crystalline form D and crystalline form E of the compound of formula I filled in No. 9 gavage capsules separately 1.3 Test Method A) Group Administration SD rats, weighing 180-200 g, after adaptation of 3-5 days, were randomly divided into 4 groups, with 4 rats in each group, and were respectively administered of crystalline form A, crystalline form B, crystalline form D and crystalline form E of the compound of formula I by intragastric administration at a dose of 20 mg/kg. The rats were fasted for 12 hours before administration and given food 4 hours after administration. Drinking water was free before and after the experiment and during the experiment.

B) Sampling

After administration, the collection time points were 0.167 h (10 min), 0.5 h, 1 h, 2 h, 4 h, 6 h, 8 h, 10 h, and 24 h. About 0.3 mL of blood was collected from the orbital venous plexus and placed in a centrifuge tube containing EDTA-K2. Stored at 4° C. Centrifuged at a condition of 4° C., 4000 rpm, 10 min within 1 h, and stored at −20° C. to be tested.

Pipetted 50 μL of plasma sample to be tested, added 300 μL of acetonitrile solution containing internal standard, shook and mixed for 5 min, centrifuged at 13000 rpm for 10 min, took 30 μL of supernatant, added 150 μL of 50% acetonitrile aqueous solution, and pipetted 1 μL for LC/MS/MS analysis and determination.

C) Detection Method

Making use of liquid chromatography-tandem mass spectrometry (LC-MS/MS), with diazepam as an internal standard (IS), protein precipitation method was used to extract the analyte and internal standard from the plasma, and reverse phase chromatography column was adopted to separate compounds and internal standard. The analyte was quantified by electrospray ionization (ESI) mode of a tandem quadrupole mass spectrometer.

TABLE 8

Chromatographic Detection Conditions

| Liquid Chromatography | Waters UPLC | | |
|---|---|---|---|
| Autosampler | FTN I-Class | | |
| Chromatographic Column | Waters BEH C18 1.7 μm, 2.1*50 mm, NO: SPZ033 | | |
| | Time(min) | Phase A: acetonitrile | Phase B: 0.1% formic acid |
| Mobile Phase | 0.30 | 40% | 60% |
| | 1.20 | 95% | 5% |
| | 1.80 | 95% | 5% |
| | 2.00 | 40% | 60% |
| | 2.80 | 40% | 60% |
| Total Flow Rate | 0.30 mL/min | | |
| Autosampler Temp | 4° C. | | |
| Column Temp | 40° C. | | |
| Injection Volume | 1 μL | | |
| Retention Time (min) | Compound of Formula I: 0.85 min, Internal Standard IS: 1.39 min | | |

TABLE 9

Mass Spectrometric Detection Conditions of Compounds and Internal Standards (the Compound of Formula I and Diazepam)

| Mass Spectrometry Model | Waters XEVO-TQS |
|---|---|
| Parameter | Optimized Value |
| Ionization Mode | (+) ESI |
| Scan Mode | Multiple Reaction Monitoring (MRM) |
| Cone (V) | 40 |
| Capillary (kV) | 3.0 |
| Source Temp (° C.) | 150 |
| Desolvation Temp (° C.) | 400 |
| Desolvation Cone (L/hr) | 750 |
| Cone (L/hr) | 150 |

TABLE 10

Precursor Ions, Fragment Ions, Collision Voltage and Collision Energy (CE)

| Compounds | Precursor Ions (m/z) | Fragment Ions (m/z) | Cone Volt (eV) | CE (eV) |
|---|---|---|---|---|
| the Compound of Formula I | 643.29 | 327.11 | 4 | 50 |
| Diazepam (IS) | 285.06 | 154.04 | 6 | 26 |

Test Results

TABLE 11

Pharmacokinetic Parameters of Test Compounds

| PK Parameters | | Crystalline Form A of the Compound of Formula I | | Crystalline Form B of the Compound of Formula I | | Crystalline Form D of the Compound of Formula I | | Crystalline Form E of the Compound of Formula I | |
|---|---|---|---|---|---|---|---|---|---|
| | | Mean | SD | Mean | SD | Mean | SD | Mean | SD |
| $T_{max}$ | (h) | 6.00 | 1.63 | 4.00 | 0.00 | 6.00 | 1.63 | 4.50 | 1.00 |
| $C_{max}$ | (µg/mL) | 481 | 211 | 1015 | 285 | 407 | 278 | 629 | 208 |
| $AUC_{(0-t)}$ | (µg*h/mL) | 4697 | 1709 | 6459 | 2829 | 3558 | 883 | 3925 | 612 |
| $AUC_{(0-\infty)}$ | (µg*h/mL) | 4964 | 1856 | 6778 | 3113 | 3783 | 969 | 4054 | 618 |
| $t_{1/2}$ | (h) | 4.93 | 0.73 | 5.30 | 0.73 | 5.20 | 0.92 | 4.61 | 0.38 |
| $MRT_{(0-t)}$ | (h) | 8.51 | 0.60 | 6.72 | 0.48 | 8.73 | 1.23 | 7.30 | 0.74 |
| $AUC_{(0-t)}$/Dose | (mL/kg) | 1035 | 399 | 1384 | 493 | 744 | 179 | 868 | 126 |
| Relative F | (%) | 100 | | 134 | | 72 | | 84 | |

What is claimed:

1. A crystalline form of the compound of formula I,

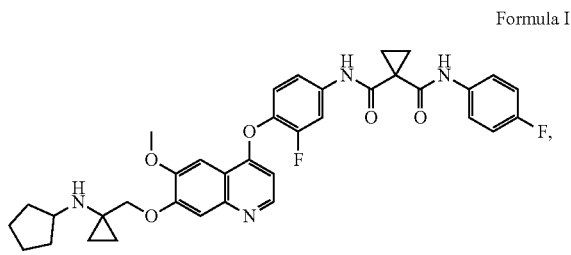 [SMILES: COc1cc2c(Oc3ccc(NC(=O)C4(C(=O)Nc5ccc(F)cc5)CC4)cc3F)ccnc2cc1OCC1(NC2CCCC2)CC1]

Formula I having a Cu Kα radiation X ray powder diffraction pattern with diffraction peaks present at 2θ angles comprising about 13.38, 15.71, 16.47, 20.15, 20.86, and 21.43 degrees, about 9.25, 10.45, 13.38, 14.03, 15.71, 16.47, 17.20, 17.85, 18.16, 18.48, 19.80, 20.15, 20.86, 21.43, 22.53, 23.43 and 24.87 degrees, about 9.25, 10.45, 12.48, 13.38, 14.03, 15.71, 16.47, 17.20, 17.85, 18.16, 18.48, 18.85, 19.80, 20.15, 20.86, 21.43, 21.79, 22.53, 23.43, 24.87, 25.47 and 29.07 degrees, or about 9.25, 9.64, 10.45, 11.27, 12.48, 13.38, 14.03, 15.71, 16.47, 17.20, 17.85, 18.16, 18.48, 18.85, 19.80, 20.15, 20.86, 21.43, 21.79, 22.53, 23.43, 24.25, 24.87, 25.47, 26.54, 26.76, 27.78, 29.07, 30.51, 31.99, 33.01, 34.65, 35.10 and 36.00 degrees.

2. A method for preparing the crystalline compound of claim 1, comprising the following steps of:

(1) mixing the compound of formula I and solvent A to obtain a solution of the compound of formula I; and (2) precipitating solid;

wherein the solvent A in step (1) comprises toluene, butanone, acetonitrile, acetonitrile and water, ethyl acetate and toluene, or acetonitrile and toluene.

3. A crystalline form of the compound of formula I,

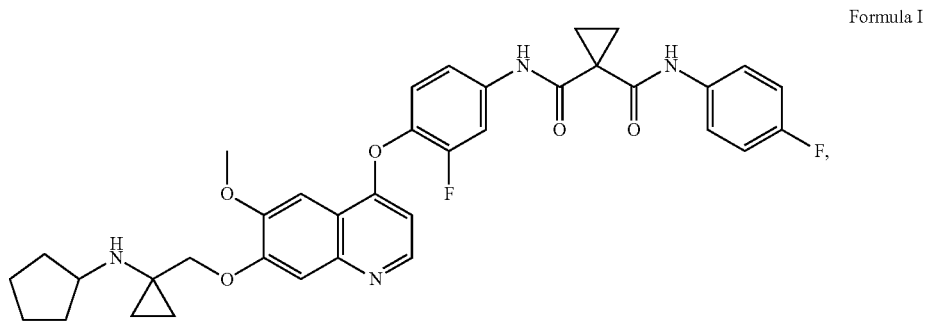 [SMILES: COc1cc2c(Oc3ccc(NC(=O)C4(C(=O)Nc5ccc(F)cc5)CC4)cc3F)ccnc2cc1OCC1(NC2CCCC2)CC1]

Formula I having a Cu Kα radiation X ray powder diffraction pattern with diffraction peaks present at 2θ angles comprising about 7.44, 8.93, 10.44 and 17.84 degrees, about 7.44, 8.93, 10.26, 10.44, 10.70, 11.17, 12.65, 12.96, 14.35, 15.49, 16.34, 17.84, 18.28, 18.73, 20.96, 21.88, 22.42, 23.03, 24.17, 25.27 and 26.16 degrees, or about 7.44, 8.93, 9.48, 10.26, 10.44, 10.70, 11.17, 11.85, 12.65, 12.96, 13.57, 14.35, 15.49, 15.75, 16.34, 17.84, 18.28, 18.73, 19.43, 20.02, 20.65, 20.96, 21.88, 22.42, 23.03, 24.17, 25.27, 25.99, 26.16 and 29.24 degrees.

4. A method for preparing the crystalline compound of claim 3 comprising the following steps of:
(1) mixing the compound of formula I and solvent B to obtain a solution of the compound of formula I; and (2) precipitating solid;
wherein the solvent B in step (1) is selected from methanol, ethanol, acetone, a mixed solvent of methanol and water, a mixed solvent of ethanol and water, a mixed solvent of acetone and water, or a mixed solvent of ethanol and butanone;
wherein the volume fraction of methanol in the mixed solvent of methanol and water is 95%;
wherein the volume fraction of ethanol in the mixed solvent of ethanol and water is 65%-95%;
wherein the volume fraction of acetone in the mixed solvent of acetone and water is 65%-95%;
wherein the volume fraction of butanone in the mixed solvent of ethanol and butanone is not more than 30%.

5. A crystalline form of the compound of formula I,

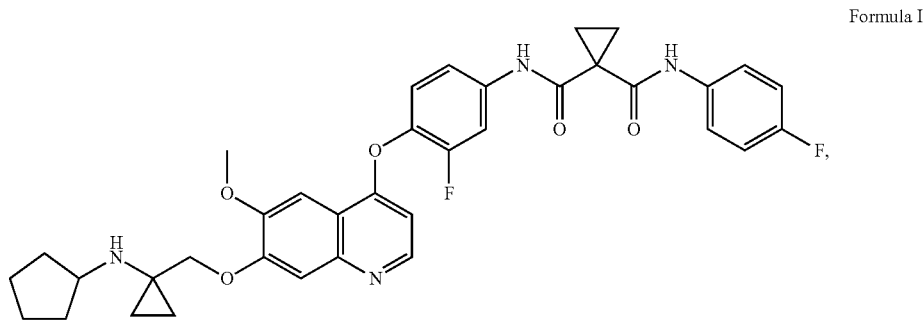 [SMILES: COc1cc2c(Oc3ccc(NC(=O)C4(C(=O)Nc5ccc(F)cc5)CC4)cc3F)ccnc2cc1OCC1(NC2CCCC2)CC1]

Formula I having a Cu Kα radiation X ray powder diffraction pattern with diffraction peaks are present at 2θ angles comprising about 7.38, 10.33 and 17.84 degrees, about 7.38, 8.80, 10.33, 11.15, 15.30, 17.84, 18.18, 19.76, 21.03 and 21.86 degrees, or about 7.38, 8.80, 10.33, 11.15, 11.71, 12.33, 12.58, 12.88, 13.50, 14.28, 15.30, 16.04, 16.33, 16.55, 17.84, 18.18, 18.43, 19.76, 21.03, 21.86, 22.83, 25.34 and 25.86 degrees.

6. A method for preparing the crystalline compound of claim 5 comprising the following steps of:
(1) mixing the compound of formula I and solvent C to obtain a solution of the compound of formula I; and
(2) precipitating solid;
wherein the solvent C in step (1) is dioxane.

7. A composition comprising the crystalline compound of claim 1.

8. A pharmaceutical composition comprising a therapeutically effective amount of a crystalline of the compound of formula I,

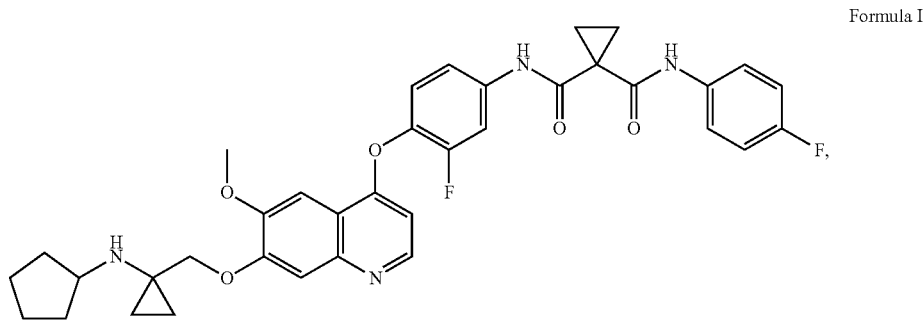 [SMILES: COc1cc2c(Oc3ccc(NC(=O)C4(C(=O)Nc5ccc(F)cc5)CC4)cc3F)ccnc2cc1OCC1(NC2CCCC2)CC1]

Formula I wherein the crystalline of the compound of formula I is the crystalline form of the compound of formula I according to claim 1.

9. A method of treating diseases mediated by c-Met kinase comprising administering an effective amount of the composition of claim 8 to a patient, wherein the disease mediated by c-Met kinase is cancer.

10. The method of claim 1, wherein the disease mediated by c-Met kinase is lung cancer.

11. A composition comprising the crystalline compound of claim 3.

12. A pharmaceutical composition comprising a therapeutically effective amount of a crystalline of the compound of formula I,

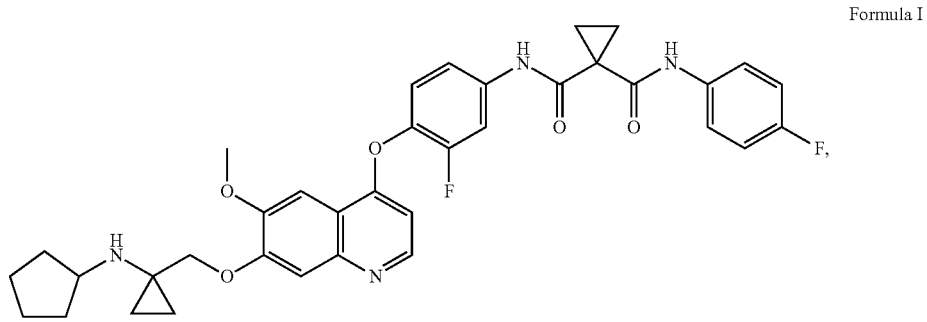 [SMILES: COc1cc2c(Oc3ccc(NC(=O)C4(C(=O)Nc5ccc(F)cc5)CC4)cc3F)ccnc2cc1OCC1(NC2CCCC2)CC1]

Formula I wherein the crystalline of the compound of formula I is the crystalline form of the compound of formula I according to claim 3.

13. A method of treating diseases mediated by c-Met kinase comprising administering an effective amount of the composition of claim 12 to a patient, wherein the disease mediated by c-Met kinase is cancer.

14. The method of claim 13, wherein the disease mediated by c-Met kinase is lung cancer.

15. A composition comprising the crystalline compound of claim 5.

16. A pharmaceutical composition comprising a therapeutically effective amount of a crystalline of the compound of formula I,

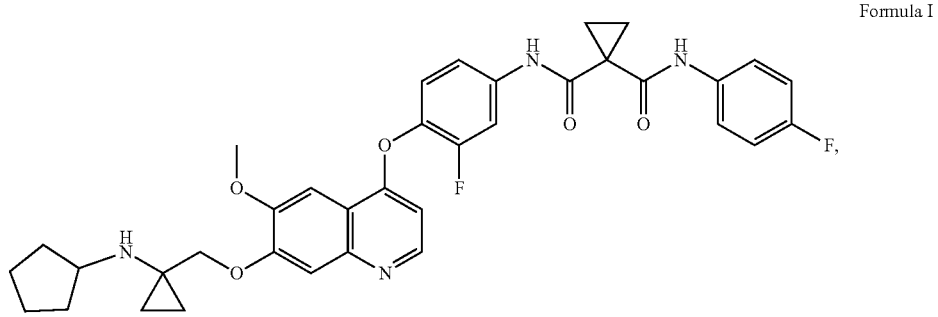 [SMILES: COc1cc2c(Oc3ccc(NC(=O)C4(C(=O)Nc5ccc(F)cc5)CC4)cc3F)ccnc2cc1OCC1(NC2CCCC2)CC1]

Formula I wherein the crystalline of the compound of formula I is the crystalline form of the compound of formula I according to claim 5.

17. A method of treating diseases mediated by c-Met kinase comprising administering an effective amount of the composition of claim 16 to a patient, wherein the disease mediated by c-Met kinase is cancer.

18. The method of claim 17, wherein the disease mediated by c-Met kinase is lung cancer.

* * * * *